United States Patent [19]

Anello

[11] 4,337,362
[45] Jun. 29, 1982

[54] CONVERSION OF HEXAFLUOROTHIOACETONE DIMER INTO HEXAFLUOROACETONE

[75] Inventor: Louis G. Anello, Hamburg, N.Y.

[73] Assignee: Allied Corporation, Morris Township, Morris County, N.J.

[21] Appl. No.: 271,456

[22] Filed: Jun. 8, 1981

[51] Int. Cl.$^3$ .............................................. C07C 45/56
[52] U.S. Cl. ................................... 568/386; 568/419; 549/89
[58] Field of Search ............... 568/393, 400, 419, 386

[56] References Cited

U.S. PATENT DOCUMENTS 3,164,637  1/1965  Anello et al. .................. 568/393
3,257,457  6/1966  Anello et al. .................. 568/393
4,057,584  11/1977  Torizuka et al. ................ 568/400

OTHER PUBLICATIONS

Middleton et al., J. Org. Chem., vol. 30, pp. 1384–1390 (1965).
Kitazuma et al., Chem. Lit., p. 267 (1973).

Primary Examiner—Natalie Trousof
Assistant Examiner—James H. Reamer
Attorney, Agent, or Firm—Thomas D. Hoffman; Jay P. Friedenson

[57] ABSTRACT

The production of hexafluoroacetone by contacting, in the liquid phase, hexafluorothioacetone dimer with at least a stoichiometric amount of an aprotic solvent selected from the group consisting of dimethylacetamide, dimethylformamide, dimethyl sulfoxide and N-methyl pyrrolidone and at least a catalytic amount of an alkali metal fluoride or a sulfonic acid having general formula $RSO_3H$ is disclosed. Dimethylformamide and dimethyl sulfoxide are the preferred aprotic solvents; KF is the preferred alkali metal fluoride; and $CH_3SO_3H$ and $pCH_3C_6H_4SO_3H$ are the preferred sulfonic acids. The production of hexafluoroacetone by contacting hexafluoropropene with elemental sulfur and a catalytic amount of an alkali metal fluoride in an aprotic solvent at a temperature of between about 40° and about 70° C. for a time sufficient to produce hexafluorothioacetone dimer combined with increasing the temperature to between about 90° and 150° C. and maintaining said temperature for a time sufficient to produce hexafluoroacetone is also disclosed.

14 Claims, No Drawings

4,337,362

CONVERSION OF HEXAFLUOROTHIOACETONE DIMER INTO HEXAFLUOROACETONE

DESCRIPTION

BACKGROUND OF THE INVENTION

The present invention relates to a method of preparing hexafluoroacetone by contacting, in the liquid phase, hexafluorothioacetone dimer with an aprotic solvent such as dimethyl sulfoxide or dimethylformamide in the presence of a catalytic amount of an alkali metal halide or organic sulfonic acid. The invention also relates to a method of preparing hexafluoroacetone by contacting, at low temperatures, hexafluoropropene with elemental sulfur and alkali metal halide in an aprotic solvent to produce hexafluorothioacetone dimer combined with reacting the dimer at elevated temperature with alkali metal fluoride in aprotic solvent to produce hexafluoroacetone.

Hexafluoroacetone is a known compound useful as an intermediate in the preparation of hexafluoropropanol and hexafluoroisobutylene, and for the preparation of compounds containing the $(CF_3)_2C-$ group.

W. J. Middleton et al. (*J. Org. Chem.,* 30, 1384–1390 (1965)) disclose preparation of hexafluoroacetone by gas phase oxidation of hexafluorothioacetone dimer with nitric oxide, NO, at 650° C., over quartz in a Vycor tube. However, this reference reports that nitric oxide does not react with hexafluorothioacetone dimer at low temperature, and that oxygen, which is also unreactive at lower temperatures, reacts with hexafluorothioacetone dimer at 650° C. to give only high conversion thereof into carbonyl fluoride and sulfur dioxide, but no hexafluoroacetone.

U.S. Pat. Nos. 3,164,637 and 3,257,457 (L. G. Anello et al.) disclose preparation of hexafluoroacetone by high temperature, gas phase fluorination of hexachloroacetone with HF in the presence of a chromium catalyst.

U.S. Patent Application Ser. No. 238,920 filed Feb. 17, 1981 (L. G. Anello et al.) discloses a process for preparing hexafluoroacetone by contacting, in the liquid phase, hexafluorothioacetone dimer with a gaseous oxidant such as $O_2$ in the presence of a catalytic amount of an alkali metal halide and an aprotic solvent such as dimethylformamide.

U.S. Patent Application Ser. No. 217,943 filed Dec. 18, 1980 (L. G. Anello et al.) discloses a process for preparing hexafluoroacetone by liquid phase reaction of hexafluorothioacetone dimer in an aprotic solvent containing alkali metal fluoride, at elevated temperature with selected metallic and non-metallic oxides.

U.S. Patent Application Ser. No. 216,035, filed Dec. 15, 1980 (L. G. Anello et al.) discloses a process for preparing hexafluoroacetone dimer by reacting hexafluoropropene with elemental sulfur and an alkali metal fluoride such as KF in an aprotic solvent such as dimethylformamide at temperatures between 25° and 100° C. However, the formation of hexafluoroacetone is not suggested or disclosed.

U.S. Pat. No. 4,057,584 (T. Touzuka et al.) discloses preparation of hexafluoroacetone by gas phase oxidation of perfluoropropene with oxygen over a fluorinated alumina catalyst.

These prior art preparations operate in the gas phase, employ high temperature, special equipment, gaseous oxidants, metallic and non-metallic oxide oxidants and specially treated catalysts.

In the presence of fluoride ion, hexafluorothioacetone dimer in dimethylformamide is in equilibrium with monomeric hexafluorothioacetone (T. Kitazume et al. *Chemistry Letters,* 267 (1973)).

Accordingly, there is a need for an economical process for the preparation of hexafluoroacetone which operates without special equipment, added oxidants or expensive catalysts.

It is an object of the present invention to provide a process for a liquid phase preparation of hexafluoroacetone without added oxidants or catalysts. This and other objects and advantages of the present invention will become obvious from the following description.

SUMMARY OF THE INVENTION

In accordance with the present invention, there is provided a method for preparing hexafluoroacetone which consists essentially of:

(a) reacting, in the liquid phase, hexafluorothioacetone dimer with at least a stoichiometric amount of an aprotic solvent selected from the group consisting of dimethylacetamide, dimethylformamide, dimethyl sulfoxide and N-methyl pyrrolidone and at least a catalytic amount of a member selected from the group consisting of LiF, NaF, KF, CsF and $RSO_3H$ wherein R is an organic radical selected from the group consisting of straight and branched chain alkyl having from one to six carbon atoms, aryl having from six to ten carbon atoms, monoalkylaryl wherein aryl contains six to ten carbon atoms and alkyl contains one to fourteen carbon atoms, and dialkylaryl wherein each alkyl group contains one to six carbon atoms;

(b) maintaining the reacting temperature above about 90° C.; and (c) recovering hexafluoroacetone.

In a preferred embodiment of the present invention there is provided a method for production of hexafluoroacetone from hexafluoropropene which consists essentially of:

(1) contacting hexafluoropropene with elemental sulfur and a catalytic amount of an alkali metal fluoride in an aprotic solvent selected from the group consisting of dimethylacetamide, dimethylformamide, dimethyl sulfoxide and N-methyl pyrrolidone while maintaining the temperature of the contacting between about 40° and 70° C. for a time sufficient to produce hexafluorothioacetone dimer;

(2) increasing the temperature to between about 90° and 150° C., and optionally adding additional alkali metal fluoride;

(3) maintaining the temperature between about 90° and 150° C. for a time sufficient to produce an effluent stream containing hexafluoroacetone; and (4) recovering hexafluoroacetone from said effluent stream.

DETAILED DESCRIPTION OF THE PRESENT INVENTION AND OF THE PREFERRED EMBODIMENTS

The present invention provides a simple synthesis of hexafluoroacetone by contacting, in the liquid phase, hexafluorothioacetone dimer with at least a stoichiometric amount of an aprotic solvent, preferably dimethylformamide or dimethyl sulfoxide and at least about a catalytic amount of a sulfonic acid having the general formula $RSO_3H$ or of an alkali metal fluoride, preferably a catalytic amount of the alkali metal fluoride, KF, while maintaining the reaction temperature above about 90° C. for a time sufficient to produce an effluent stream containing hexafluoroacetone. The hexafluoroacetone can conveniently be recovered from the effluent stream by conventional fractional distillation techniques at sufficiently high pressures and sufficiently low temperatures to condense hexafluoroacetone.

Copending U.S. Patent Application Ser. No. 238,920 filed Feb. 27, 1981 (L. G. Anello et al.) discloses preparation of hexafluoroacetone by reacting gaseous oxidants such as $O_2$ with a solution of hexafluorothioacetone dimer in an aprotic solvent such as dimethylformamide containing a catalytic amount of an alkali metal fluoride such as KF. Copending U.S. Application Ser. No. 217,943, filed Dec. 18, 1980 (L. G. Anello et al.) discloses preparation of hexafluoroacetone by reacting metallic oxides such as HgO or non-metallic oxides such as $KIO_3$ with a solution of hexafluorothioacetone dimer in an aprotic solvent such as dimethylformamide containing an alkali metal fluoride such as HF. Surprisingly it was discovered that hexafluoroacetone was produced by reacting hexafluorothioacetone dimer with an aprotic solvent selected from a group consisting of dimethylacetamide, dimethylformamide, dimethyl sulfoxide and N-methyl pyrrolidone containing a catalytic amount of a sulfonic acid having the general formula $RSO_3H$ or an alkali metal fluoride such as KF at reaction temperatures of at least about 90° C. No oxidant such as $O_2$, HgO or $KIO_3$ previously thought necessary was required.

Temperatures of at least about 90° C., preferably about 100° to about 150° C., more preferably about 100° to about 125° C. are adequate for the production of hexafluoroacetone. Contact times are not critical. Contact times of about 5–8 hours are preferred.

Among the aprotic solvents found useful for the present invention are dialkyl alkanamide wherein each alkyl is a straight or branched chain group containing one to six carbons and wherein alkanamide contains one to ten carbon atoms, dialkyl sulfoxide wherein each alkyl group is a straight or branched chain group containing one to six carbon atoms, carbocyclic sulfoxides having four to six carbon atoms such as $(CH_2)_4SO$, $(CH_2)_5SO$ and $(CH_2)_6SO$ and N-alkyl pyrrolidones wherein the alkyl group is a straight or branched chain group having one to ten carbons.

The preferred aprotic solvents for the present invention are dimethylacetamide, dimethylformamide, dimethyl sulfoxide and N-methyl pyrrolidone. Dimethylformamide and dimethyl sulfoxide are more preferred.

Among the catalysts found useful in the present invention are sulfonic acids having the formula $RSO_3H$ wherein R is an organic radical selected from the group consisting of straight and branched chain alkyl having from one to six carbon atoms, aryl having six to ten carbon atoms, monoalkylaryl wherein aryl contains six to ten carbon atoms and alkyl contains one to fourteen carbon atoms and dialkylaryl wherein each alkyl contains one to six carbon atoms and aryl contains six to ten carbon atoms and the alkali metal fluorides LiF, NaF, KF, and CsF. The preferred sulfonic acid catalysts are $CH_3SO_3H$, $p-CH_3C_6H_4SO_3H$ and the preferred alkali metal fluoride is KF. While hydrated sulfonic acids such as hydrated $p-CH_3C_6H_4SO_3H$ may be employed, it is preferred to use anhydrous sulfonic acids such as anhydrous $CH_3SO_3H$ and anhydrous $p-CH_3C_6H_4SO_3H$. For economic reasons KF is most preferred.

The catalytic amount of $RSO_3H$ and alkali metal fluoride found useful in the present reaction varies from at least about 0.06 moles to about 1.0 moles of $RSO_3H$ or alkali metal fluoride per mole of hexafluorothioacetone dimer. While an amount in excess of 1.0 mole of catalyst such as $RSO_3H$ or alkali metal fluoride such as KF per mole of hexafluorothioacetone dimer is effective in producing hexafluoroacetone, the preferred molar ratio of catalyst to hexafluorothioacetone dimer is at least about 0.06:1 to about 1.0:1.0.

While at least about a stoichiometric amount (2 moles) of aprotic solvent such as dimethylformamide is required per mole of hexafluorothioacetone dimer, it was found convenient to use at least a volume of aprotic solvent equivalent to the volume of hexafluorothioacetone dimer. A ten fold volume excess of aprotic solvent is preferred. For economic considerations, it is preferred to employ the aprotic solvents dimethylformamide or dimethyl sulfoxide.

It is considered within the scope of the present invention that inert solvents such as dimethylsulfone or tetramethylene sulfone could be added to the reaction mixture of hexafluorothioacetone dimer, aprotic solvent and catalyst such as $CH_3SO_3H$ or KF. By the term "inert" is meant unreactive with hexafluorothioacetone dimer, aprotic solvent or catalyst of the present invention.

In a preferred embodiment of the present invention, hexafluoroacetone is prepared in a single reaction vessel directly, without isolating hexafluorothioacetone dimer by reacting hexafluoropropene with elemental sulfur and an alkali metal fluoride catalyst such as KF in an aprotic solvent such as dimethylformamide at temperatures between about 40° and about 70° C. for a time sufficient to form hexafluorothioacetone dimer. Then the temperature of the reaction is raised to at least about 90°, preferably 100° to 125° C. and optionally additional KF is added. The reaction is maintained at least about 90° C., preferably about 100° to 125° C. for a time sufficient to product hexafluoroacetone which is collected in a cold trap and recovered via fractional distillation at reduced pressure.

The following examples illustrate and describe but do not limit the present invention.

EXPERIMENTAL EXAMPLE 1

Into a 250 mL, 3 neck flask fitted with a thermometer, stirrer, and a −20° C. cooled condenser connected to a dry ice-acetone cooled trap was charged 50 g (0.137 mole) of

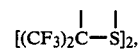

1 g anhydrous KF and 50 mL dimethyl sulfoxide. The mixture was heated to reflux over a 24 hour period. Reflux temperature dropped from 110° C. to 90° C. over the course of reaction. The effluent gases from the reaction vessel were collected in the dry ice-acetone cold trap. The cold trap yielded 13.5 g of crude product which by GC analysis indicated that 11.3 g (0.068 mole) was hexafluoroacetone and 0.7 g (0.011 mole) was dimethyl sulfide. The yield of hexafluoroacetone was 25% based on starting hexafluorothioacetone dimer.

EXAMPLE 2

Following the procedure of Example 1, 50 g (0.137 mole) of

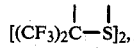

2.5 g anhydrous KF and 100 mL dimethylformamide were heated from 100° to 150° C. over a 5 hour period. The mixture turned quite dark and about 9 g sulfur precipitated from solution. The cold trap yielded 18.5 g crude product which by GC analysis indicated that 5.2 g (0.045 mole) was $CF_3COF$, 10 g (0.06 mole), was $CF_3COCF_3$ and 2.4 g (0.011 mole) was $(CF_3)_3CH$. The yield of hexafluoroacetone was 22% based on starting hexafluorothioacetone dimer.

EXAMPLE 3

Following the procedure of Example 1, 100 g (0.274 mole)

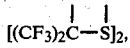

3.5 g anhydrous KF, 60 g (2.02 mole) trioxane (α-trioxymethylene), 50 mL DMF and 100 mL dimethylacetamide were heated from 100° C. to 143° C. over a 25 hour period. The cold trap yielded 29.4 g crude product which on GC analysis indicated that 15 g (0.09 mole) was $CF_3COCF_3$, 4.4 g (0.027 mole) was $(CF_3)_2C=CH_2$ and 5.0 g (0.023 mole) was $(CF_3)_3CH$. The yield of hexafluoroacetone and hexafluoroisobutylene was 16.4% and 4.9% respectively based on starting hexafluorothioacetone dimer.

EXAMPLE 4

Following the procedure of Example 1, 50 g (0.137 mole)

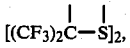

50 mL dimethylacetamide and 2 g anhydrous KF were heated from 100° C. to 153° C. over a 5 hour period. The cold trap yielded 17 g crude product which on GC analysis indicated that 10 g (0.06 mole) was $CF_3COCF_3$. The yield of hexafluoroacetone was 21.7% based on starting hexafluorothioacetone dimer.

EXAMPLE 5

Following the procedure of Example 1, 50 g (0.137 mole)

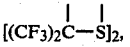

3 g $CH_3SO_3H$ and 80 mL of dimethylformamide were heated from 100° C. to 150° C. over a six hour period. The cold trap yielded 20 g crude product which on GC analysis indicated that 17 g (0.102 mole) was $CF_3COCF_3$. The yield of hexafluoroacetone was 37.2% based on starting hexafluorothioacetone dimer.

EXAMPLE 6

The procedure of Example 5 is followed excepting that $p-CH_3C_6H_4SO_3H$ is substituted from $CH_3SO_3H$. The hexafluoroacetone is recovered from a dry-ice-acetone trap.

EXAMPLES 7–24

In the following Examples the process of Example 1 is repeated in the same apparatus excepting that the aprotic solvent and catalyst are varied as indicated in the following table.

| Example | Aprotic Solvent | Catalyst |
|---|---|---|
| 7 | DMF[1] | LiF |
| 8 | DMF | NaF |
| 9 | DMF | CsF |
| 10 | DMAC[2] | LiF |
| 11 | DMAC | NaF |
| 12 | DMAC | CsF |
| 13 | DMAC | $p-CH_3C_6H_4SO_3H$ |
| 14 | DMAC | $CH_3SO_3H$ |
| 15 | DMSO[3] | LiF |
| 16 | DMSO | NaF |
| 17 | DMSO | CsF |
| 18 | DMSO | $CH_3SO_3H$ |
| 19 | DMSO | $p-CH_3C_6H_4SO_3H$ |
| 20 | N-methyl pyrrolidone | LiF |
| 21 | N-methyl pyrrolidone | NaF |
| 22 | N-methyl pyrrolidone | CsF |
| 23 | N-methyl pyrrolidone | $CH_3SO_3H$ |
| 24 | N-methyl pyrrolidone | $p-CH_3C_6H_4SO_3H$ |

[1] DMF is dimethylformamide
[2] DMAC is dimethylacetamide
[3] DMSO is dimethyl sulfoxide

EXAMPLE 25

Into a 500 mL 3-neck flask equipped with a thermometer, mechanical stirrer, gas inlet tube and a water-cooled condenser was charged 48 g (1.50 moles) sulfur, 87.0 g (1.50 moles) of anhydrous potassium fluoride and 200 mL dimethylformamide. The mixture was heated to 40°–45° C. and 218 g (1.45 moles) hexafluoropropene added during 2-¼ hours. An additional 16 g (0.50 mole) sulfur was added and 88 g (0.58 mole) of hexafluoropropene added during a 2 hour period at 55° C. Total sulfur reacted was 64 g (2.0 moles) and total hexafluoropropene added was 306 g (2.04 moles). The contents of the flask were poured into a separatory funnel and the lower layer, 352.5 g, was phase separated from the upper layer. The lower layer was chilled to −10° C. and dimethylformamide solvent separated from the crystallized hexafluorothioacetone dimer. The recovered dimer was fractionally distilled to give 285 g (0.78 mole) of dimer for a 76% conversion and yield.

EXAMPLE 26

The procedure of Example 25 is followed excepting that hexafluorothioacetone dimer is not isolated. Additional KF is added and the temperature is raised to 100° to 125° C. The hexafluoroacetone is recovered from a dry ice-acetone trap.

EXAMPLES 27–29

The procedure of Example 25 is followed excepting that the aprotic solvent is dimethylacetamide in Example 27, dimethyl sulfoxide in Example 28 and N-methyl pyrrolidone in Example 29.

What is claimed is:

1. A method of preparing hexafluoroacetone which consists essentially of:
   (a) reacting, in the liquid phase, hexafluorothioacetone dimer with at least about a stoichiometric amount of an aprotic solvent selected from the group consisting of dimethylacetamide, dimethylformamide, dimethyl sulfoxide and N-methyl pyrrolidone and at least a catalytic amount of a member selected from the group consisting of LiF, NaF, KF, CsF and $RSO_3H$ wherein R is an organic radical selected from the group consisting of straight and branched chain alkyl having from one to six carbon atoms, aryl having from six to ten carbon atoms, monoalkylaryl wherein aryl contains six to ten carbon atoms and alkyl contains one to fourteen carbon atoms and dialkylaryl wherein each alkyl group contains one to six carbon atoms;
   (b) maintaining the reacting temperature above about 90° C.; and
   (c) recovering hexafluoroacetone.

2. The method of claim 1 wherein the aprotic solvent is dimethyl sulfoxide.

3. The method of claim 1 wherein the aprotic solvent is dimethylformamide.

4. The method of claim 2 or 3 wherein a catalytic amount of KF is added.

5. The method of claim 2 or 3 wherein a catalytic amount of $CH_3SO_3H$ is added.

6. The method of claim 2 or 3 wherein a catalytic amount of $p\text{-}CH_3C_6H_4SO_3H$ is added.

7. The method of claim 2 or 3 wherein the volume ratio of said dimer:the aprotic solvent is about 1:10.

8. The method of claim 2 or 3 wherein a catalytic amount of KF is added and wherein the molar ratio of said dimer:KF is at least about 1:0.06 to about 1:1.

9. The method of claim 2 or 3 wherein the hexafluoroacetone is recovered from a gaseous effluent stream containing same by condensing said effluent stream under sufficiently high pressure and sufficiently low temperature to condense hexafluoroacetone.

10. The method of claim 2 or 3 wherein the reacting temperature is in the range of about 100° to about 150° C.

11. The method of clam 2 or 3 wherein the reacting temperature is in the range of about 100° to about 125° C.

12. A method for production of hexafluoroacetone from hexafluoropropene which consists essentially of:
   (1) contacting hexafluoropropene with elemental sulfur and a catalytic amount of an alkali metal fluoride in an aprotic solvent selected from the group consisting of dimethylacetamide, dimethylformamide, dimethyl sulfoxide and N-methyl pyrrolidone while maintaining the temperature of the contacting between about 40° and 70° C. for a time sufficient to produce hexafluorothioacetone dimer;
   (2) increasing the temperature to between about 90° and 150° C. and optionally adding additional alkali metal fluoride;
   (3) maintaining the temperature between about 90° and 150° C. for a time sufficient to produce an effluent stream containing hexafluoroacetone; and
   (4) recovering hexafluoroacetone from said effluent stream.

13. The method of claim 12 wherein the aprotic solvent is dimethylformamide and wherein the alkali metal fluoride is KF which is added in steps (1) and (2) and wherein the temperature in step (3) is maintained between about 100° and 125° C.

14. The method of claim 12 wherein the aprotic solvent is dimethylformamide and wherein the alkali metal fluoride is KF which is added only in step (1) and wherein the temperature of step (3) is maintained between about 100° and 125° C.

* * * * *